United States Patent [19]
Michelotti et al.

[11] Patent Number: 5,945,565
[45] Date of Patent: Aug. 31, 1999

[54] PROCESS FOR THE MANUFACTURE OF ACETONYLBENZAMIDES

[75] Inventors: Enrique Luis Michelotti, Fort Washington; Heather Lynnette Rayle, Doylestown; Randall Wayne Stephens, Perkasie; William Joseph Zabrodski, Lansdale, all of Pa.

[73] Assignee: Rohm and Haas Company, Philadelphia, Pa.

[21] Appl. No.: 09/177,149

[22] Filed: Oct. 22, 1998

Related U.S. Application Data

[62] Division of application No. 08/873,131, Jun. 10, 1997, Pat. No. 5,874,466.
[60] Provisional application No. 60/020,519, Jun. 28, 1996.
[51] Int. Cl.$^6$ .................................................. C07C 51/58
[52] U.S. Cl. ............................................ 562/861; 562/864
[58] Field of Search .................................... 562/495, 861, 562/864; 564/256

[56] References Cited

U.S. PATENT DOCUMENTS

| | | |
|---|---|---|
| 4,822,902 | 4/1989 | Carley et al. . |
| 5,021,454 | 6/1991 | Sharma . |
| 5,304,572 | 4/1994 | Michelotti et al. . |

FOREIGN PATENT DOCUMENTS

| | | |
|---|---|---|
| 3615762 | 11/1987 | Germany . |

*Primary Examiner*—Robert W. Ramsuer
*Assistant Examiner*—Joseph Murray
*Attorney, Agent, or Firm*—Clark R. Carpenter

[57] ABSTRACT

Novel routes for the preparation of acetonylbenzamides are provided by the reaction of an amine and acyl chloride. Novel routes to various intermediates used in the manufacture of acetonylbenzamides are also disclosed.

2 Claims, No Drawings

PROCESS FOR THE MANUFACTURE OF ACETONYLBENZAMIDES

This application is a divisional application of Ser. No. 08/873,131 filed Jun. 10, 1997 now patented, U.S. Pat. No. 5,874,466, which is based on Provisional Application Ser. No. 60/020,519 filed Jun. 28, 1996.

The present invention provides a method for the manufacture of acetonylbenzamides. More specifically, the present invention provides a method for the production of acetonylbenzamides which requires fewer steps and reduces the number of raw materials required in the manufacture of these compounds.

Acetonylbenzamides are known to possess fungicidal properties, see for example U.S. Pat. Nos. 4,822,902, 5,021,454 and 5,304,572. These patents disclose various methods for producing acetonylbenzamides; however, there is a continuing need to produce acetonylbenzamides in a more economical manner.

The present invention provides a method for producing acetonylbenzamides of Formula I:

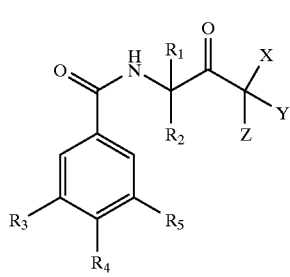

from the reaction of an acyl chloride of the Formula II:

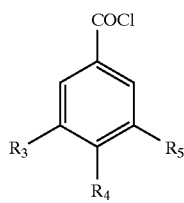

and an amine of Formula III

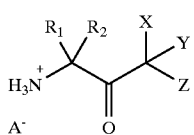

wherein A is a monovalent anion, including but not limited to, Cl, Br, I, $HSO_4$, $CH_3SO_3$, and $ClO_4$;

$R_1$ and $R_2$ are each independently hydrogen, $(C_1-C_4)$ alkyl, $(C_2-C_4)$alkenyl and $(C_2-C_6)$alkynyl, provided that $R_1$ and $R_2$ are not both hydrogen;

$R_3$, $R_4$ and $R_5$ are each independently halo, $(C_1-C_4)$alkyl, $(C_2-C_4)$alkenyl, $(C_2-C_6)$alkynyl, $(C_1-C_4)$alkoxy, amino, $CH=NOCH_3$ and cyano; and X, Y and Z are each independently hydrogen, halo, cyano, thiocyanato, isothiocyanato, and $(C_1-C_4)$ alkylsulfonyloxy, provided that at least one of them is not hydrogen.

As used throughout the specification, the substituents X, Y and Z are understood to be interchangeable and not rigidly fixed as depicted in the figures.

Another embodiment of the present invention provides a method for preparing the compound of Formula I (depicted hereinabove) comprising the reaction of a benzoic acid of formula IV

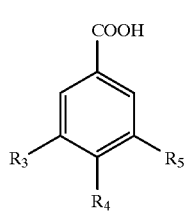

with methanesulfonyl chloride; the reaction product of the benzoic acid and methanesulfonyl chloride further reacted with an amine of Formula III

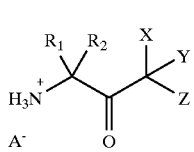

wherein A is a monovalent anion including but not limited to Cl, Br, I, $HSO_4$, $CH_3SO_3$, and $ClO_4$;

$R_1$ and $R_2$ are each independently hydrogen, $(C_1-C_4)$ alkyl, $(C_2-C_4)$alkenyl or $(C_2-C_6)$alkynyl, provided that $R_1$ and $R_2$ are not simultaneously hydrogen;

$R_3$, $R_4$ and $R_5$ are each independently halo, $(C_1-C_4)$alkyl, $(C_2-C_4)$alkenyl, $(C_2-C_6)$alkynyl, $(C_1-C_4)$alkoxy, amino, $CH=NOCH_3$ or cyano; and X, Y and Z are each independently hydrogen, halo, cyano, thiocyanato, isothiocyanato, or $(C_1-C_4)$ alkylsulfonyloxy, provided that at least one of them is not hydrogen.

Another embodiment of the present invention is a method for producing the compound of Formula III (depicted hereinabove): comprising the reaction of

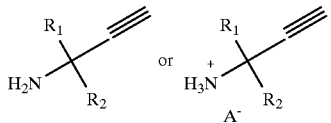

wherein A is a monovalent anion including but not limited to Cl, Br, I, $HSO_4$, $CH_3SO_3$, and $ClO_4$;
with trifluoroacetic anhydride to provide the compound of Formula VI;

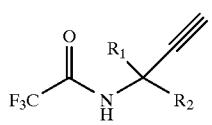

then chlorinating the compound of Formula VI to provide the compound of Formula VII;

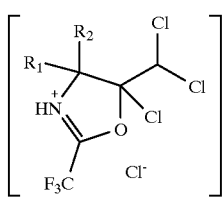

VII and reacting the compound of Formula VII with an aqueous acid such as H₂SO₄, HCl, or HBr to provide the compound of Formula III. R1, R2, X, Y, and Z are understood to have the same definition as used hereinabove.

Alkyl, either by itself or as part of any substituent listed above, means straight and branched alkyl groups, for example, methyl, ethyl, isopropyl and hexyl. Haloalkyl means alkyl substituted with one or more halogen atoms, for example, chloroethyl, chloromethyl or trifluoromethyl. Alkylsulfonyloxy is understood to be $(C_1–C_4)alkyl.SO_3^-$; cyano is —CN; thiocynato is —SCN.

Method I

The present invention provides the reaction of an acyl chloride of Formula II, with an amine of Type I (a compound of Formula III wherein X, Y and Z contains 2 chlorine atoms and 1 hydrogen atom)

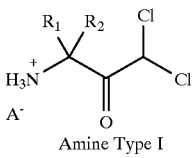

Amine Type I wherein A is defined hereinabove, in the presence of an amine such as triethylamine (TEA) or a pyridine to form the compound of Formula A. Selective removal of one chlorine by hydrogen in the presence of palladium converts the resulting N-dichloroacetonylbenzamide to the N-chloroacetonylbenzamide of Formula Z.

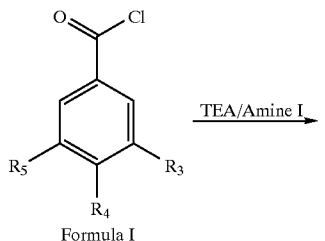
Formula I

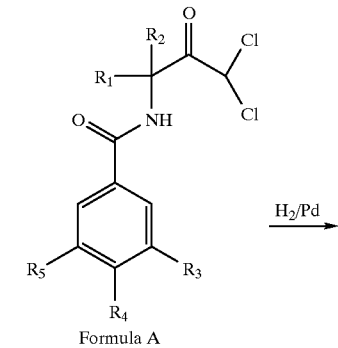
Formula A

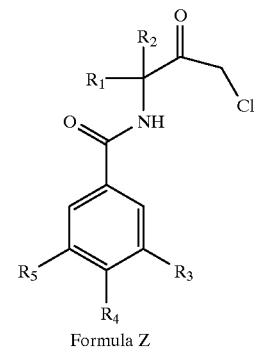
Formula Z wherein $R_1$, $R_2$, $R_3$, $R_4$ and $R_5$ are defined above.

Alternatively, the reaction of the corresponding acyl chloride of Formula II can be performed with an amine of Type II (a compound of Formula III wherein X, Y and Z contains 2 hydrogen atoms and 1 chlorine atom)

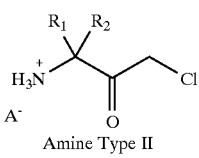

Amine Type II wherein A is defined hereinabove, in the presence of an amine such as TEA or pyridine to form directly the corresponding N-chloroacetonylbenzamide.

The synthesis of amines of Type I and Type II is shown in the following scheme:

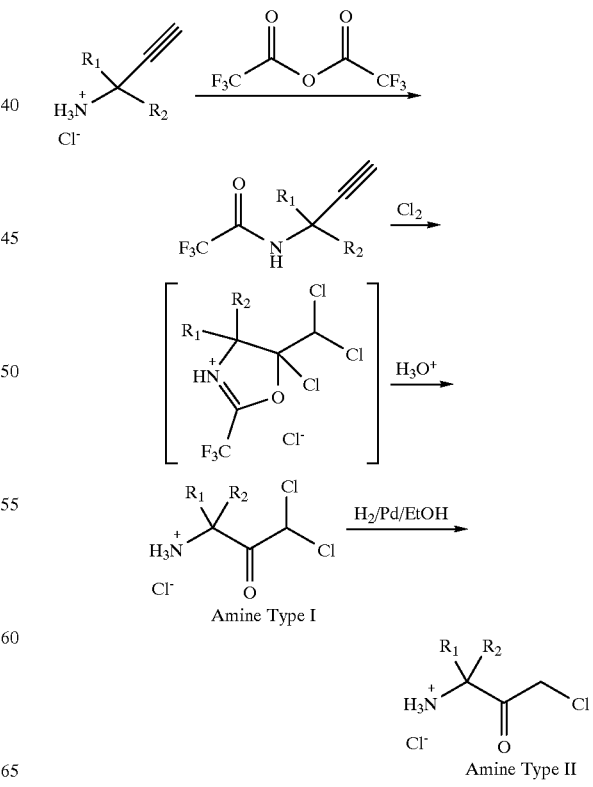

Scheme: Synthesis of amines of Type I and Type II

The resulting amine products will be referred to throughout this specification as amines of Type I or Type II, respectively.

Method II

The amidation reaction can also be carried out by reacting the corresponding acyl chloride of Formula II with an amine of Type I in the presence of an inorganic base such as sodium bicarbonate using water as a solvent in the presence of an organic cosolvent such as toluene or hexane yielding the corresponding N-dichloroacetonylbenzamide of Formula A. Selective removal of one chlorine atom by hydrogen in the presence of palladium converts the resulting N-dichloroacetonylbenzamide to the N-chloroacetonylbenzamide of Formula Z.

Alternatively, the reaction of the corresponding acyl chloride of Formula II can be performed with an amine of Type II in the presence of an inorganic base such as sodium bicarbonate using water as a solvent in the presence of an organic cosolvent such as toluene or hexane yielding directly the corresponding N-chloroacetonylbenzamide of Formula Z.

Method III

The present invention also provides the reaction of the mixed anhydride formed from the corresponding benzoic acid of Formula IV with methanesulfonyl chloride in the presence of a base such as TEA, followed by reaction with an amine of Type II yielding the corresponding N-acetonylbenzamide as shown below:

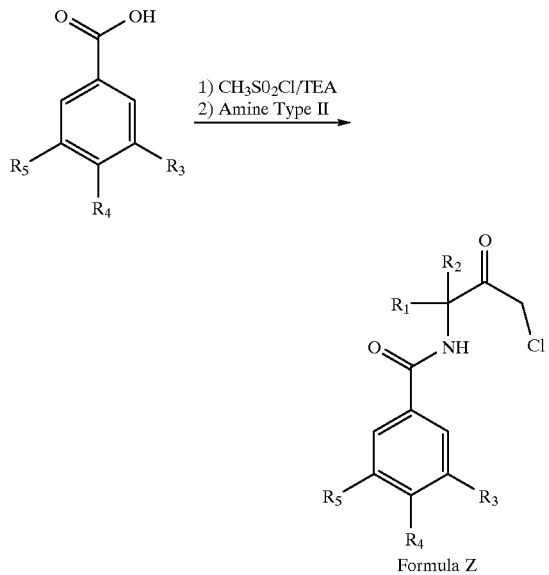

Formula Z

Alternatively, the mixed anhydride is reacted with an amine of Type I followed by selective removal of one chlorine by hydrogen in the presence of palladium to form the corresponding acetonylbenzamide of Formula Z.

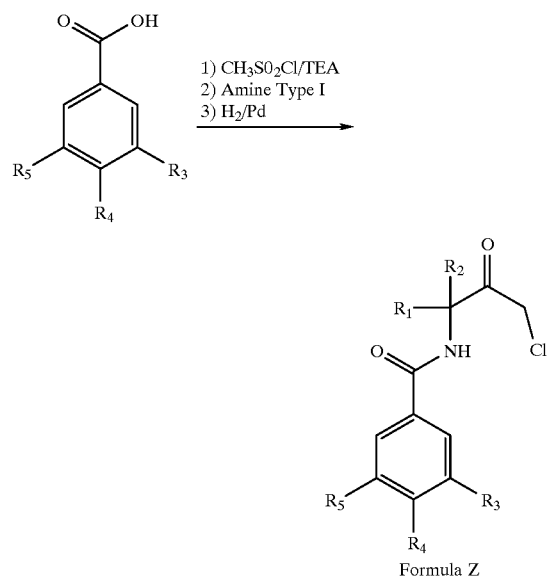

Formula Z where $R_1$, $R_2$, $R_3$, $R_4$, and $R_5$ are the same as described hereinabove.

Method IV

In the synthesis of the desired N-acetonylbenzamides novel synthetic routes to various benzoyl chlorides are also disclosed.

For example commercially available p-toluoyl chloride is chlorinated in the presence of a Lewis acid catalyst. Preferred catalysts include aluminum (III) chloride or antimony (V) chloride. The reaction is run to partial conversion, from about 30 to 50% by weight of p-toluoyl chloride to prevent the formation of overchlorinated products. The mono- and dichlorinated acyl chlorides are separated by distillation; the 3-chloro-p-toluoyl chloride obtained is recycled for further chlorination.

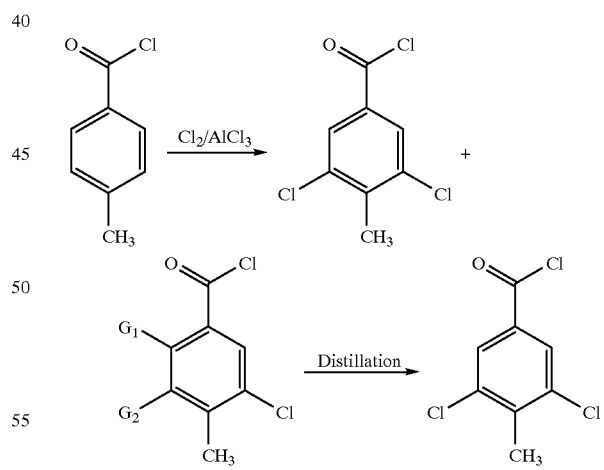

wherein $G_1$ and $G_2$ are independently selected from hydrogen and chlorine.

This process is preferable to that described in DE 3615762 for two reasons. First, the preferred catalysts employed are much more selective than the iron chloride used in the prior art. The chlorination of p-toluoyl chloride under the conditions described in the German disclosure afford the 3,5- and 2,5-dichlorinated acid chlorides in a 5.4:1 ratio, along with several percent of the monochloride and large amounts of 2,3,5-trichlorinated product. However, we found that when the chlorination is performed using aluminum (III) chloride or antimony (V) chloride as catalyst, 3,5- to 2,5-dichlorinated product ratios from 10:1 to 20:1, preferably 15:–17:1 are typically obtained. Second, the concept of running the chlorination to low conversion and recycling the monochloro intermediate has not been previously disclosed. The chlorination is completed before significant quantities of overchlorinated byproducts begin to form. Unconverted 3-chloro-p-toluoyl chloride is isolated and recycled for further chlorination. As a result, the overall yield of desired 3,5-dichloro-p-toluoyl chloride is significantly improved, typically affording yields of 3,5-dichloro-p-toluoyl chloride in greater than 70 percent, preferably 80 percent, yield based upon the amount of the starting p-toluoyl chloride. Additionally, the volume of organic waste generated is reduced.

A novel route for the synthesis of the previously undisclosed 4-amino-3-chloro-5-(methoxyiminomethyl)benzoyl chloride comprises the conversion

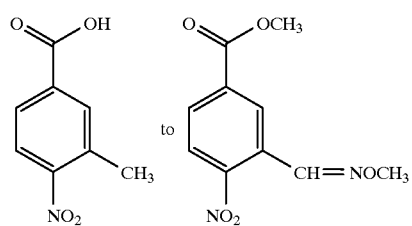

by sequential bromination, displacement of bromine by an acetoxy group, hydrolysis to the alcohol, oxidation to the aldehyde, and conversion to the methoxyimino Compound X; followed by the reduction of the nitro group to corresponding amine and chlorination of the resulting aniline to provide 4-amino-3-chloro-5-(methoxyiminomethyl)benzoyl chloride.

Schematically the described reaction is as follows:

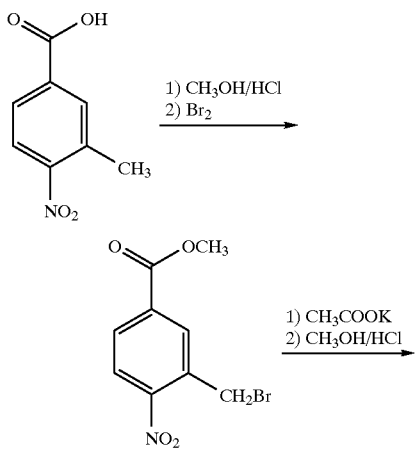

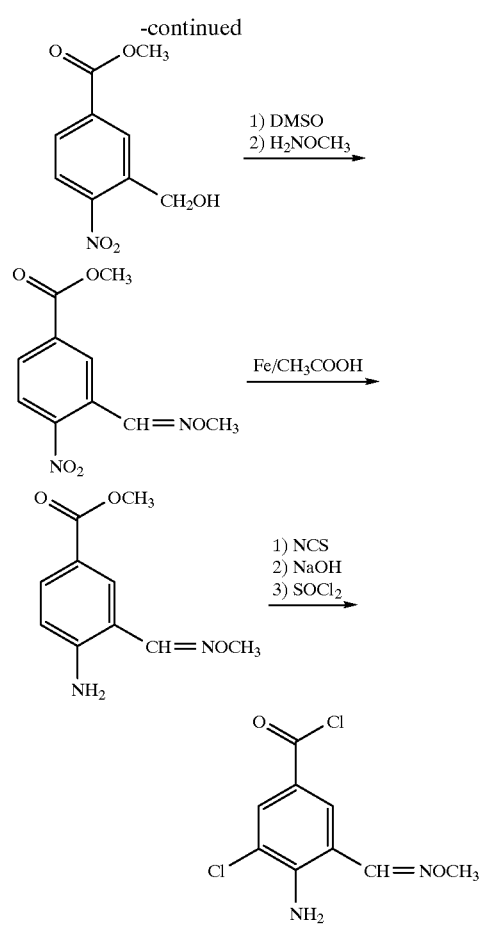

wherein DMSO is dimethylsulfoxide and NCS is N-chlorosuccinimide.

The following examples are illustrative of the present invention.

EXAMPLE 1

The following compounds of Formula Z were prepared by the method described in the specification.

| Compound | Method | $R_1$ | $R_2$ | $R_3$ | $R_4$ | $R_5$ |
|---|---|---|---|---|---|---|
| 1 | 2 | $CH_3$ | $CH_2CH_3$ | Cl | $CH_3$ | Cl |
| 2 | 3 | $CH_3$ | $CH_2CH_3$ | Cl | $NH_2$ | Cl |
| 3 | 1 | $CH_3$ | $CH_2CH_3$ | Cl | H | Cl |
| 4 | 1 | $CH_3$ | $CH_2CH_3$ | Cl | $NH_2$ | $CH=NOCH_3$ |

EXAMPLE 2

Preparation of 3,5-dichloro-4-methylbenzoyl chloride (Method IV)

a) A 1-liter jacketed kettle was equipped with a chiller, overhead stirrer, thermometer, and connections to a chlorine tank and a caustic scrubber. The kettle was charged with p-toluoyl chloride (78.9 g, 0.5 mole) and 1,2-dichloroethane (432 mL) to prepare a 1M solution. Aluminum trichloride (80.8 g, 0.6 mole) was added, and the resulting red-brown mixture was cooled with stirring until the temperature reached 3–5° C. Chlorine was introduced at a rate sufficient to keep the reaction temperature below 10° C. When the dichlorinated products comprised at least 50% of the reaction mixture, the addition was halted. The reaction mixture was purged with nitrogen and slowly quenched by pouring into chilled 4M aqueous hydrochloric acid. The organic layer was collected and dried over sodium sulfate. The solvent was removed under reduced pressure; the residue (96–103 g) was distilled under vacuum through a 20-tray distillation column. 3-Chloro-4-methylbenzoyl chloride distilled at approximately 120° C. at 23 mm Hg. 3,5-Dichloro-4-methylbenzoyl chloride distilled at about 130° C. at 16 mm Hg.

b) A jacketed kettle was equipped with a chiller, overhead stirrer, thermometer, and connections to a chlorine tank and a caustic scrubber. The kettle was charged with one part by weight p-toluoyl chloride and 9.5 parts dichloromethane. Aluminum trichloride (0.95 parts) was added, and the resulting red-brown mixture was cooled with agitation to 3–5° C. Chlorine (0.95 parts) was introduced at a sufficient rate to keep the reaction temperature below 10° C. The kettle was held at 0–5° C. for 6 hours. The reaction mixture was purged with nitrogen and slowly quenched by transferring into an agitated and chilled hydrochloric acid solution (7.2 parts) while maintaining the temperature below 5° C. Agitation was stopped and the lower organic layer was recovered. The solvent was removed by distillation.

The residue was distilled using a packed column at reduced pressure. The 3-chloro-4-methylbenzoyl chloride distilled at 134° C. @ 15 mm Hg, and the expected 3,5-dichloro-4-methylbenzoyl chloride distilled at 155° C. @ 15 mm Hg. The overall recovery was 92%. The product contained 55% of the expected 3,5-dichloro-4-methylbenzoyl chloride. The 3-chloro-4-methylbenzoyl chloride produced was recycled to the reactor for further chlorination. Intermediate cuts were redistilled until the 3,5-dichloro-4-methylbenzoyl chloride was a 92–95% pure product.

Recycle of 3-chloro-4-methylbenzoyl chloride

A jacketed kettle was equipped with a chiller, overhead stirrer, thermometer, and connections to a chlorine tank and a caustic scrubber. The kettle was charged with the previously prepared 3-chloro-4-methylbenzoyl chloride (1 part) and dichloromethane (6.8 parts). Aluminum trichloride (0.8 parts) was added, and the resulting red-brown mixture was cooled with agitation to 3–5° C. Chlorine (0.37 parts) was introduced at a sufficient rate to keep the reaction temperature below 10° C. The reactor was held at 0–5° C. for 6 hours. The reaction mixture was purged with nitrogen and slowly quenched by transfering into an agitated and chilled hydrochloric acid solution (4.4 parts) while maintaining the temperature below 5° C. Agitation was stopped and the lower organic layer was recovered. The solvent was removed by distillation.

The residue was distilled using a packed column at reduced pressure. The 3-chloro-4-methylbenzoyl chloride distilled at 134° C. @ 10 mm Hg, and the expected 3,5-dichloro-4-methylbenzoyl chloride distilled at 155° C. @ 10 mm Hg. The overall recovery was 90%. The product contained 72% of the expected 3,5-dichloro-4-methylbenzoyl chloride. Intermediate cuts were redistilled until the 3,5-dichloro-4-methylbenzoyl chloride was a 92–95% pure product.

EXAMPLE 3

Preparation of Amine Type I and Amine Type II
($R_1$=$CH_3$, $R_2$=$CH_2CH_3$)

a) Preparation of N-[3-(3-methyl-1-pentynyl)]trifluoroacetamide

In a 3 liter, four-necked, round-bottomed flask fitted with a mechanical stirrer, nitrogen inlet and thermometer was placed 234 g (1.75 mole) of 3-amino-3-methyl-1-pentyne hydrochloride and 1,000 mL of methylene chloride. To the resulting well-stirred mixture was added slowly 354 g (3.51 mole) of triethylamine (TEA) dropwise, keeping the temperature below 30° C. After the addition was completed, the reaction mixture was stirred 120 minutes followed by dropwise addition of 334.5 g (1.59 mole) of trifluoroacetic anhydride dissolved in 500 mL of methylene chloride at such a rate to keep the reaction temperature at 0° C. After the addition was completed the reaction mixture was stirred at room temperature overnight and concentrated in vacuo. The resulting slurry was washed with ethyl ether. The ethyl ether layer was washed sequentially with water, saturated aqueous sodium bicarbonate and brine, dried over anhydrous magnesium sulfate, treated with activated charcoal, and filtered through Celite™. The solvent was eliminated under reduced pressure. The resulting crude product was treated with cold pentane, filtered, and dried yielding 255.5 g (83%) of the expected N-[3-(3-methyl-1-pentynyl)]trifluoroacetamide as a white solid.

b) Preparation of 5-chloro-5-(dichloromethyl)-4-ethyl-4-methyl-2-trifluoromethyloxazoline hydrochloride In a 5 L, four-necked, round-bottomed flask fitted with a mechanical stirrer, a thermometer, and a gas inlet was dissolved 255.5 g (1.32 mole) of N-[3-(3-methyl-1-pentynyl)]trifluoroacetamide in 4,000 mL of methylene chloride. The resulting mixture was cooled to −30° C. and 235 g of chlorine was bubbled in over a 2 hour period. When the addition was completed the reaction mixture was stirred at −30° C. during 30 minutes and warmed to room temperature. The crude reaction mixture was evaporated in the rotary evaporator yielding the expected 5-chloro-5-(dichloromethyl)-4-ethyl-4-methyl-2-trifluoromethyloxazoline hydrochloride which was used as such in the next step.

c) Preparation of 3-amino-1,1-dichloro-3-methyl-2-pentanone hydrochloride (Amine Type I, $R_1$=$CH_3$; $R_2$=$CH_2CH_3$)

The 5-chloro-5-(dichloromethyl)-4-ethyl-4-methyl-2-trifluoromethyloxazoline hydrochloride prepared in the preceding step was dissolved in 1800 mL of methanol, 72 mL of water, and 190 mL of concentrated hydrochloric acid, warmed to 50° C., and stirred at that temperature overnight. The crude reaction mixture was cooled and poured into an ice/water/ethyl ether mixture. The phases were separated and the ether layer was extracted once with water. The ether was saved (organic I). The combined aqueous layers were washed once with ethyl ether, and the organic layer was combined with organic I (organic II). The aqueous layer was neutralized with saturated aqueous sodium bicarbonate and extracted twice with ethyl ether. The combined ether layers were washed with water, brine, dried over anhydrous magnesium sulfate, treated with activated charcoal, and filtered through Celite™. To the resulting colorless solution was bubbled in anhydrous hydrogen chloride keeping the temperature below 20° C. The resulting white solid was filtered and dried yielding 124.8 g of the expected 3-amino-1,1-dichloro-3-methyl-2-pentanone hydrochloride as a white solid. The ethyl ether filtrate was combined with organic II and concentrated in vacuo; the resulting residue (150 g) was taken in a mixture of methanol/water/concentrated hydrochloric acid and heated at 50° C. over the weekend. The previously described workup yielded another 51 g of 3-amino-1,1-dichloro-3-methyl-2-pentanone hydrochloride. The total amount obtained was 175.8 g (61% yield).

d) Preparation of 3-amino-1-chloro-3-methyl-2-pentanone hydrochloride (Amine Type II, $R_1$=$CH_3$; $R_2$=$CH_2CH_3$)

In a 2 L Parr™ bottle was placed 41 g of 3-amino-1,1-dichloro-3-methyl-2-pentanone hydrochloride, 0.8 g of 10% palladium over charcoal, and 400 mL of ethanol. The resulting mixture was shaken in a Parr™ apparatus at 50 psi for 3 hours. The crude reaction mixture was filtered through Celite™ and evaporated in vacuo yielding a viscous oil, which was taken in 300 to 400 mL of ethyl acetate and stirred at room temperature for several hours. The expected 3-amino-1-chloro-3-methyl-2-pentanone hydrochloride crystallized as a white solid; 300 mL of hexane was added to the resulting suspension and filtered yielding 34 g (98%) of the expected 3-amino-1-chloro-3-methyl-2-pentanone hydrochloride.

The reaction was repeated starting with 41 g; 41 g; and 51 g of 3-amino-1,1-dichloro-3-methyl-2-pentanone hydrochloride yielding a total of 132.1 g (90% overall yield) of 3-amino-1-chloro-3-methyl-1-pentanone hydrochloride.

EXAMPLE 4

Preparation of 4-amino-3,5-dichloro-N-(3-chloro-1-ethyl-1-methyl-2-oxopropyl)benzamide (Method III)

In a 100 mL three-necked round-bottomed flask fitted with a mechanical stirrer, nitrogen inlet and thermometer was placed 0.62 g (3 mmol) of 4-amino-3,5-dichlorobenzoic acid, 20 mL of tetrahydrofuran, and 1.52 g (15 mmol) of triethylamine. To the resulting well-stirred mixture was added 0.4 g (3.3 mmol) of methanesulfonyl chloride dropwise while keeping the reaction temperature at −25° C. The resulting suspension was stirred at −25° C. for 30 minutes, after which 0.7 g (3.8 mmol) of 3-amino-1-chloro-3-methyl-2-pentanone hydrochloride was added slowly over a 45 minute period. After the addition was complete, the reaction mixture was stirred at −25° C. for an additional 60 minutes. The cooling bath was removed; the reaction mixture was allowed to warm to room temperature and stirred for 3 hours. The reaction mixture was poured into a mixture of water and ethyl acetate. The phases were separated and the aqueous layer was extracted several times with ethyl acetate. The combined organic phases were washed sequentially with water, saturated aqueous sodium bicarbonate, and water, then dried over anhydrous magnesium sulfate. The resulting solution was treated with charcoal and filtered through Celite™. The solvent was removed using a rotary evaporator, yielding 0.84 g of 4-amino-3,5-dichloro-N-(3-chloro-1-ethyl-1-methyl-2-oxopropyl)benzamide as a white solid, mp 134–138° C.

EXAMPLE 5

Preparation of 3,5-dichloro-N-(3-chloro-1-ethyl-1-methyl-2-oxopropyl)benzamide (Method I)

To a well-stirred mixture of 0.62 g (3.3 mmol) of 3-amino-1-chloro-3-methyl-2-pentanone hydrochloride and 25 mL of methylene chloride in a 50 mL round-bottomed flask, placed in an ice bath, was added dropwise 0.91 g (9 mmol) triethylamine. After 15 minutes 0.44 g (3 mmol) 3,5-dichlorobenzoyl chloride in methylene chloride (approximately 5 mL) was added dropwise. The mixture was stirred while the temperature was maintained between 0° C. to 5° C. for 1 hour. The reaction mixture was warmed to room temperature and stirred for 3 hours. The reaction mixture was then poured into a mixture of ethyl acetate and water. The mixture separated into phases, an organic and an aqueous phase. The organic phase was washed sequentially with saturated aqueous sodium bicarbonate (1×50 mL), water (1×50 mL), 2.5% aqueous hydrochloric acid (1×50 mL), and water (1×50 mL). The organic layer was dried over anhydrous magnesium sulfate, treated with charcoal and filtered through Celite™ and the solvent was removed in a rotary evaporator yielding 0.6 g of 3,5-dichloro-N-(3-chloro-1-ethyl-1-methyl-2-oxopropyl)benzamide as a white solid (mp 159–161° C.).

EXAMPLE 6

Preparation of 3,5-dichloro-N-(3-chloro-1-ethyl-1-methyl-2-oxopropyl)-4-methylbenzamide (Method II using Amine Type II, $R_1$=$CH_3$; $R_2$=$CH_2CH_3$)

To a well-stirred solution of 1.1 g (13.1 mmol) sodium bicarbonate in 15 mL water was added solid 3-amino-1-chloro-3-methyl-2-pentanone hydrochloride (1 g, 5.4 mmoles) portionwise. To the resulting solution was added 15 mL of hexane followed by dropwise addition of a solution of 3,5-dichloro-4-methylbenzoyl chloride (1.2 g, 5.4 mmol) in 1 mL of tetrahydrofuran. Another 15 mL of hexane was added, and the resulting mixture was stirred at room temperature for 2 hours. The reaction mixture was filtered, and the resulting white solid was dried in a vacuum oven yielding 1.1 g of 3,5-dichloro-N-(3-chloro-1-ethyl-1-methyl-2-oxopropyl)-4-methylbenzamide as a white solid (mp 159–161° C.).

EXAMPLE 7

Preparation of 3,5-dichloro-N-(3,3-dichloro-1-ethyl-1-methyl-2-oxopropyl)-4-methylbenzamide (Method II using Amine Type I, $R_1$=$CH_3$; $R_2$=$CH_2CH_3$, followed by hydrogenolysis)

a) Preparation of 3,5-dichloro-N-(3,3-dichloro-1-ethyl-1-methyl-2-oxopropyl)-4-methylbenzamide In a 100 mL three-necked round bottomed flask was placed 0.93 g of 3-amino-1,1-dichloro-3-methyl-2-pentanone hydrochloride and 5 mL of water. To the resulting solution was added 0.76 g of sodium bicarbonate followed by 20 mL of ethyl acetate. To the resulting well-stirred mixture was added 0.94 g of 3,5-dichloro-4-methylbenzoyl chloride dissolved in 20 mL of ethyl acetate at room temperature over a period of 5 minutes. After the addition was complete the reaction mixture was stirred at room temperature for 1 hour. The two phases were separated and the organic layer was washed with water (2×25 mL), brine (1×25 mL), dried over anhydrous magnesium sulfate and the solvent removed using a rotary evaporator yielding 1.34 g (84% yield) of 3,5-dichloro-N-(3,3-dichloro-1-ethyl-1-methyl-2-oxopropyl)-4-methylbenzamide as a white solid. This solid was used as such in the following step.

b) Preparation of 3,5-dichloro-N-(3-chloro-1-ethyl-1-methyl-2-oxopropyl)-4-methylbenzamide 3,5-Dichloro-N-(3,3-dichloro-1-ethyl-1-methyl-2-oxopropyl)-4-methylbenzamide (1.34 g) prepared in the previous step, ethanol (50 mL) and 5% palladium over charcoal (100 mg) were placed in a hydrogenation bottle and hydrogenated in a Parr™ apparatus (50 psi, room temperature) for 3 hours. The reaction mixture was filtered through Celite™ and the solvent eliminated under pressure, to yield a crude product. The crude product was triturated with hexane, yielding after filtration 1.1 g (91% yield) of 3,5-dichloro-N-(3-chloro-1-ethyl-1-methyl-2-oxopropyl)-4-methylbenzamide as a white solid.

EXAMPLE 8

Preparation of 4-amino-3-chloro-5-methoxyiminomethyl-N-(3-chloro-1-ethyl-1-methyl-2-oxopropyl)benzamide (Method II using Amine Type II, $R_1$=$CH_3$; $R_2$=$CH_2CH_3$)

a) Preparation of methyl 3-methyl-4-nitrobenzoate

In a 5-liter three-necked round-bottomed flask equipped with a reflux condenser, overhead stirrer and gas inlet, was placed 300 g of 3-methyl-4-nitrobenzoic acid and 3 l of methanol. To the resulting well-stirred solution was bubbled in 20.8 g of hydrogen chloride and the resulting mixture was refluxed for 3 hours. The reaction mixture was cooled to room temperature and allowed to stand overnight. The expected methyl 3-methyl-4-nitrobenzoate precipitated as light yellow crystals, which were collected by suction filtration yielding after drying 259.3 g. This solid was used as such in the next step.

b) Preparation of methyl 3-bromomethyl-4-nitrobenzoate

In a 5-liter three-necked round-bottomed flask equipped with a reflux condenser, overhead stirrer, addition funnel and nitrogen inlet, was placed 220 g of methyl 3-methyl-4-nitrobenzoate, 2 l of anhydrous carbon tetrachloride and 4 g of benzoyl peroxide. To the resulting solution, irradiated with a 275 watt UV light, was added 198 g of bromine dropwise over a period of 2 hours at reflux. After the addition was complete the reaction mixture was refluxed for an additional 60 hours. The reaction mixture was cooled to room temperature. The solid which formed was separated by suction filtration. This solid (159.1 g) consisted of the expected methyl 3-bromomethyl-4-nitrobenzoate with minor amounts of the starting material. The mother liquors together with another 220 g of methyl 3-methyl-4-nitrobenzoate and 4 g of benzoyl peroxide were returned to the flask and treated with 198 g of bromine as described above. After the addition was complete the reaction mixture was refluxed another 96 hours, cooled to room temperature and the resulting solid separated by filtration yielding another 252 g of methyl 3-bromomethyl-4-nitrobenzoate. The solids were combined yielding a total of 411.1 g of methyl 3-bromomethyl-4-nitrobenzoate with minor amounts of the starting methyl 3-methyl-4-nitrobenzoate and methyl 3-dibromomethyl-4-nitrobenzoate. This solid was used as such in the next step.

c) Preparation of methyl 3-acetoxymethyl-4-nitrobenzoate

In a 5-liter three-necked round-bottomed flask equipped with a reflux condenser, overhead stirrer and nitrogen inlet, was placed 411 g of the previously prepared methyl 3-bromomethyl-4-nitrobenzoate, 441 g of anhydrous potassium acetate and 2 l of glacial acetic acid. The resulting mixture was refluxed for 4 hours, cooled to room temperature and stirred overnight. The solvent was removed in a rotary evaporator and the resulting light yellow solid treated with a mixture of 2 l of ethyl acetate and 1 l of water. The organic phase was separated, washed with water (3×400 mL), brine (1×400 mL) dried over anhydrous magnesium sulfate and the solvent removed using a rotary evaporator. The crude reaction mixture was triturated with hexane and filtered yielding 318 g of the expected methyl 3-acetoxymethyl-4-nitrobenzoate. This compound was used as such in the next step.

d) Preparation of methyl 3-hydroxymethyl-4-nitrobenzoate

In a 5-liter three-necked round-bottomed flask equipped with a reflux condenser, overhead stirrer and nitrogen inlet, was placed 318 g of the previously prepared methyl 3-acetoxymethyl-4-nitrobenzoate and 3.2 l of anhydrous methanol. To the resulting solution was bubbled in 40 g of hydrogen chloride and the resulting mixture was refluxed for 3 hours. After cooling to room temperature the solvent was removed using a rotary evaporator yielding 273 g of methyl 3-hydroxymethyl-4-nitrobenzoate as a yellow solid containing traces of methanol, which was used as such in the next step.

e) Preparation of methyl 3-formyl-4-nitrobenzoate

In a 5-liter four-necked round-bottomed flask 1.5 l of methylene chloride was cooled to −78° C. Oxalyl chloride (164 g, 1.29 moles) was added slowly, followed by dropwise addition of 202 g (2.59 moles) of dry dimethylsulfoxide in 125 mL of methylene chloride, keeping the temperature below −70° C. After the addition was complete the reaction mixture was stirred at −78° C. for 30 minutes and 273 g (1.29 moles) of previously prepared methyl 3-hydroxymethyl-4-nitrobenzoate dissolved in 250 mL of methylene chloride was added dropwise. The reaction mixture was stirred an additional 30 minutes. Triethylamine (392 g 3.88 moles) in 125 mL of methylene chloride was added dropwise keeping the temperature below −65° C. The reaction mixture was warmed up slowly to room temperature and stirred overnight. The solvent was removed using a rotary evaporator and the resulting solid treated with a mixture of 2 l of ethyl acetate and 1 l of water. The organic phase was separated, filtered through diatomaceous earth, and washed sequentially with dilute aqueous hydrochloric acid (2×250 mL), water (2×250 mL), saturated aqueous sodium bicarbonate (2×250 mL), water (2×200 mL), brine (1×200 mL) and dried over anhydrous magnesium sultate. The solvent was removed using a rotary evaporator. The crude reaction mixture was triturated with hexane and filtered yielding 234.1 g of the expected methyl 3-formyl-4-nitrobenzoate as a yellow solid. This compound was used as such in the next step.

f) Preparation of methyl 3-methoxyiminomethyl-4-nitrobenzoate

To a well stirred mixture of 195 g of methyl 3-formyl-4-nitrobenzoate, 1 l methylene chloride and 370 mL of water was added sequentially 77.6 g of methoxylamine hydrochloride, 76.2 g of sodium acetate and 6.8 g of tetra-n-butylammonium hydrogen sulfate. The resulting mixture was stirred overnight at room temperature, then diluted with 2 l of ethyl ether. The organic phase was separated and washed sequentially with water (1×500 mL), 2% aqueous hydrochloric acid (2×500 mL), water (2×250 mL), and brine (1×250 mL); then dried over anhydrous magnesium sulfate. The solvent was removed using a rotary evaporator yielding 218.6 g of the expected methyl 3-methoxyiminomethyl-4-nitrobenzoate as a reddish oil that solidified upon standing, and which was used as such in the next step.

g) Preparation of methyl 4-amino-3-methoxyiminomethylbenzoate

In a 5-liter three-necked round-bottomed flask was placed 0.9 l of 5% aqueous acetic acid and 157 g (2.8 moles) of iron. To the resulting well-stirred mixture was added 166.6 g (0.7 moles) of the previously prepared methyl 3-methoxyiminomethyl-4-nitrobenzoate dissolved in 0.9 l of ethyl acetate followed by dropwise addition of 0.9 l of acetic acid while keeping the temperature below 35° C. The resulting mixture was stirred at 35° C. for 30 minutes and filtered through diatomaceous earth. The filtrate was poured into 5 l of water. The aqueous phase was separated and washed with ethyl ether (2×500 mL). The combined organic layers were washed sequentially with water (4×500 mL), saturated aqueous sodium bicarbonate (2×500 mL), water (2×500 mL), and brine (1×400 mL). The organic layer was dried over anhydrous magnesium sulfate and the solvent removed using a rotary evaporator yielding 130 g of the expected methyl 4-amino-3-methoxyiminomethylbenzoate.

h) Preparation of methyl 4-amino-3-chloro-5-methoxyiminomethylbenzoate

In a 2-liter three-necked round-bottomed flask was placed 106 g (0.51 moles) of the previously prepared 4-amino-3-methoxyiminomethylbenzoate and 500 mL of acetonitrile. The resulting mixture was heated at 70° C. and 75.2 g (0.56 moles) of N-chlorosuccinimide was added portionwise while keeping the temperature below 80° C. After the addition was complete the reaction mixture was refluxed for 1 hour. The reaction mixture was cooled to room temperature and the solvent eliminated in a rotary evaporator. The crude product was dissolved in 5 l of ethyl acetate. The organic solution was washed with water (3×500 mL) and then brine, dried over magnesium sulfate. The reaction mixture was concentrated in a rotary evaporator to a slurry, triturated with hexane and filtered yielding the expected methyl 4-amino-3-chloro-5-methoxyiminomethylbenzoate as a yellow solid. This reaction was repeated using the same amounts yielding a total of 210.5 g of methyl 4-amino-3-chloro-5-methoxyiminomethylbenzoate, which was used as such in the next step.

i) Preparation of 4-amino-3-chloro-5-methoxyiminomethylbenzoic acid

In a 5-liter three-necked round-bottomed flask was placed 210 g (0.86 moles) of the previously prepared 4-amino-3-chloro-5-methoxyiminomethylbenzoate, 1.7 l of methanol and 462 g (1.73 moles) of 15% aqueous sodium hydroxide. The resulting mixture was refluxed for 3 hours, after which the reaction mixture was stirred overnight at room temperature. The reaction mixture was concentrated using a rotary evaporator. The crude reaction mixture was dissolved in 2 l of water. The resulting aqueous solution was washed once with 500 mL of ethyl acetate, cooled in an ice bath and acidified to pH=2 with concentrated hydrochloric acid. The expected 4-amino-3-chloro-5-methoxyiminomethylbenzoic acid precipitated as a light yellow solid which was separated by suction filtration. The filter cake was washed with a 1:2 mixture of ethyl ether and hexane yielding after drying 185.2 g (94% yield).

j) Preparation of 4-amino-3-chloro-5-methoxyiminomethylbenzoyl chloride

In a 5-liter three-necked round-bottomed flask was placed 180 g of the previously prepared 4-amino-3-chloro-5-methoxyiminomethylbenzoic acid, 2 l of toluene, 3 mL of dimethylformamide and 104 g (64 mL) of thionyl chloride. The resulting mixture was heated at 70° C. for 2 hours, filtered while hot and the solvent removed using a rotary evaporator yielding 178.1 g of the expected 4-amino-3-chloro-5-methoxyiminomethylbenzoyl chloride.

k) Preparation of 4-amino-3-chloro-5-methoxyiminomethyl-N-(3-chloro-1-ethyl-1-methyl-2-oxopropyl)benzamide In a 5-liter three-necked round bottomed flask was placed 93 g of 3-amino-1-chloro-3-methyl-2-pentanone hydrochloride and 885 mL of water. To the resulting solution were added 138.6 g of sodium bicarbonate followed by 500 mL of ethyl acetate. To the resulting well-stirred mixture was added 123.5 g of 4-amino-3-chloro-5-methoxyiminomethylbenzoyl chloride dissolved in 1000 mL of ethyl acetate at room temperature over a period of 50 minutes. After the addition was complete the reaction mixture was stirred at room temperature for 1 hour. The two phases were separated and the organic layer was washed with water (2×500 mL), brine (1×500 mL), dried over anhydrous magnesium sulfate and the solvent eliminated in a rotary evaporator yielding the crude product as a brown oil. This oil was passed through a short Silica Gel column using methylene chloride as elution solvent. Evaporation of the solvent yielded 133.3 g of the expected 4-amino-3-chloro-5-methoxyiminomethyl-N-(3-chloro-1-ethyl-1-methyl-2-oxopropyl)benzamide as an off-white solid (mp 140–141° C.).

We claim:

1. A method for producing 4-amino-3-chloro-5-(methoxyiminomethyl)benzoyl chloride comprising the conversion of

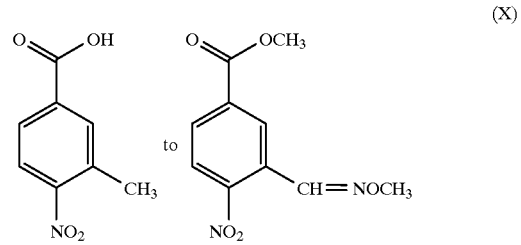

by sequential bromination, reaction of the brominated compound with an alkali metal acetate, hydrolysis to the alcohol, oxidation to the aldehyde and subsequent reaction with a methoxyamine to produce the methoxyimino Compound X; followed by the reduction of the nitro group to the corresponding amine and chlorination of the resulting aniline compound to provide 4-amino-3-chloro-5-(methoxyiminomethyl)benzoyl chloride.

2. The compound 4-amino-3-chloro-5-(methoxyiminomethyl)benzoyl chloride.

* * * * *